(12) United States Patent
Reu et al.

(10) Patent No.: US 9,389,220 B2
(45) Date of Patent: Jul. 12, 2016

(54) IN VITRO ASSAY SYSTEMS AND METHODS FOR IDENTIFYING ANTI-CANCER AGENTS

(71) Applicant: THE CLEVELAND CLINIC FOUNDATION, Cleveland, OH (US)

(72) Inventors: Frederic J. Reu, Beachwood, OH (US); Sergei Vatolin, Bay Village, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 14/609,516

(22) Filed: Jan. 30, 2015

(65) Prior Publication Data

US 2015/0212066 A1    Jul. 30, 2015

Related U.S. Application Data

(60) Provisional application No. 61/933,431, filed on Jan. 30, 2014.

(51) Int. Cl.
| | |
|---|---|
| *G01N 33/567* | (2006.01) |
| *G01N 33/574* | (2006.01) |
| *C12M 3/00* | (2006.01) |
| *G01N 33/50* | (2006.01) |
| *C12N 5/0775* | (2010.01) |

(52) U.S. Cl.
CPC .......... *G01N 33/5011* (2013.01); *C12N 5/0663* (2013.01); *G01N 33/5073* (2013.01); *G01N 33/5067* (2013.01)

(58) Field of Classification Search
CPC .......... G01N 33/5011; G01N 33/5044; G01N 2500/10; G01N 33/5067; G01N 37/567; G01N 33/574; C12N 5/0663; C12M 3/00
USPC ....................... 435/7.2, 7.23, 287.1
See application file for complete search history.

(56) References Cited

U.S. PATENT DOCUMENTS

2010/0255999 A1* 10/2010 Mitsiades .............. C12M 35/08
506/2

FOREIGN PATENT DOCUMENTS

| WO | 8103663 A1 | 12/1981 |
|---|---|---|
| WO | 2008095165 A2 | 8/2008 |
| WO | 2010124207 A1 | 10/2010 |
| WO | 2013063588 A1 | 5/2013 |

OTHER PUBLICATIONS

Fujita et al. Tumor-Stromal Interactions With Direct Cell Contacts Enhance Proliferation of Human Pancreatic Carcinoma Cells; Cancer Science, vol. 100, No. 12 (2009) pp. 2309-2317.*
Vatolin et al. A Novel In Vitro Three Organ Assay System Identifies a Small Molecule Ubiquitin Analog With In Vivo Activity Against Myeloma; 56th ASH Annual Meeting and Exposition (Dec. 6, 2014) downloaded from https://ash.confex.com/ash/2014/webprogram/Paper76861.html on Feb. 9, 2016.*
Astashkina et al., "Critical Analysis of 3-D Organoid in Vitro Cell Culture Models for High-Throughput Drug Candidate Toxicity Assessments", Advanced Drug Delivery Reviews, 69-70, 2014, pp. 1-18.
Ebrahimkhani et al., "Bioreactor Technologies to Support Liver Function In Vitro", Advanced Drug Delivery Reviews, 69-70, 2014, pp. 132-157.
Kostadinova et al., "A Long-Term Three Dimensional Liver Co-Culture System for Improved Prediction of Clinically Relevant Drug-Induced Hepatotoxicity", Toxicology and Applied Pharmacology, 268, 2013, pp. 1-16.
Roth et al., "The Application of 3D Cell Models to Support Drug Safety Assessment: Opportunities & Challenges", Advanced Drug Delivery Reviews, 69-70, 2014, pp. 179-189.
International Search Report and Written Opinion for PCT/US2015/013651, mailed May 19, 2015, pp. 1-13.

* cited by examiner

*Primary Examiner* — Paul Martin
(74) *Attorney, Agent, or Firm* — Tarolli, Sundheim, Covell & Tummino LLP

(57) ABSTRACT

The present disclosure relates generally to drug discovery and development and, more particularly, to in vitro assay systems and methods for selecting lead anti-cancer agents for subsequent testing in human and non-human subjects. The present disclosure allows filtering for candidate anti-cancer agents that are not inactivated by liver enzymes, are able to diffuse through cell layers, are not toxic to bone marrow cells, retain anti-cancer activity in the context of stromal support, and are effective after time-limited exposure mimicking non-hepatic clearance by kidneys and other mechanisms.

20 Claims, 3 Drawing Sheets

IN VITRO ASSAY SYSTEMS AND METHODS FOR IDENTIFYING ANTI-CANCER AGENTS

RELATED APPLICATION

This application claims the benefit of U.S. Provisional Patent Application Ser. No. 61/933,431, filed Jan. 30, 2014, the entirety of which is hereby incorporated by reference for all purposes.

TECHNICAL FIELD

The present disclosure relates generally to drug discovery and development and, more particularly, to in vitro assay systems and methods for selecting lead anti-cancer agents for subsequent testing in human and non-human subjects.

BACKGROUND

Cells represent the primary building blocks of higher biological systems, such as tissues, organs, as well as entire multicellular organisms. In higher organisms, e.g., mammals, cells often interact with one another for such important biological functions as transmitting signals and building macrostructures, including tissues. Cell interaction may also profoundly influence various disease states, such as infectious, immune and autoimmune disorders, primary site or metastatic cancers, thus it is often of great importance to study any specific biological problem in its in vivo context, or at least in a system that somewhat mimics or approximates its in vivo context.

However, due to many technical and theoretical difficulties, doing so is not always possible or practical. For example, in the field of new drug development, traditional studies tend to focus on the effect of a candidate compound on a specific cell type of interest, in isolation from the general biological context in which the cell functions. In other words, this type of study, for various reasons, intentionally or accidentally omits the microenvironment in which the cell operates, and thus it may not come as a surprise when one identifies a promising drug candidate in the initial in vitro study, only to find in later stage drug development that the candidate drug fails in clinical trial.

One case on point is drug development for cancer treatment. Historically, the early stages of anti-cancer drug development have involved high-throughput screening of large libraries of compounds for potential in vitro activity against tumor cell lines. In these screening modalities, tumor cells are studied in conventional in vitro systems, where tumor cells are cultured in isolation from any other cell types with which they might interact in the in vivo local microenvironment of the tumor. These conventional screening strategies have included, e.g., the NCI60 panel of 60 tumor cell lines, which has been the basis for the anti-cancer screening program of the Developmental Therapeutics Program of the National Cancer Institute (NCI). Overall, the NCI60 panel and other similar screening programs in both academia and industry have been useful in identifying candidate anti-cancer compounds, many (but not all) of which have translated in clinical applications for systemic chemotherapy of human malignancies.

Unfortunately, systemic chemotherapy using anti-cancer compounds for human neoplasia, which may have been identified using such methods, is generally not curative. In fact, a key challenge identified in the oncology field for several years now is the contrast between the remarkable in vitro anti-tumor activity exhibited in the past by many conventional and investigational anti-cancer agents, and their typically less impressive clinical activity of these agents when they were eventually tested in clinical trials.

This kind of problem is by no means a unique phenomenon of cancer drug development. Most (if not all) drugs do not affect a single cell type; instead, they act on many different types of living cells in an entire organism. Thus, the ultimate efficacy of a drug not only depends on its effect on its target cell, but also the influence of the microenvironment on the target cell. Thus arguably, all drug development faces the same issue, maybe to different extents. This problem is particularly acute in modern day drug development, where years (if not decades) of research and tremendous amount of human and financial resources are typically devoted to the process.

SUMMARY

The present disclosure relates generally to drug discovery and development and, more particularly, to in vitro assay systems and methods for selecting lead anti-cancer agents for subsequent testing in human and non-human subjects.

One aspect of the present disclosure relates to an in vitro assay system for identifying a candidate anti-cancer agent. The system can comprise a first well, a removable insert, and a second well. The first well can have an interior volume defined by a bottom surface and at least one side wall extending from the bottom surface to an open upper end. The first well can comprise a liver-derived layer that contains a test anti-cancer agent and is in direct contact with the bottom surface, one or more bone marrow cells adjacent the liver-derived layer, and a volume of cell culture media. The removable insert can be suspended within the interior volume of the first well and immersed in the volume of cell culture media. The removable insert can include a lower surface comprising a semi-permeable membrane and at least one side wall extending from the lower surface to define an insert chamber, at least one tumor cell located in the insert chamber and being configured to express a detectable marker, and at least one support cell located in the insert chamber. The second well can have an interior volume defined by a bottom surface and at least one side wall extending from the bottom surface to an open upper end. The second well can comprise a liver-derived layer that is free of the test anti-cancer agent and is in direct contact with the bottom surface, one or more bone marrow cells adjacent the liver-derived layer, and a volume of cell culture media.

Another aspect of the present disclosure relates to an in vitro method for identifying a candidate anti-cancer agent. One step of the method can include determining, after a first period of time, the viability of one or more bone marrow cells present in a first well. The first well can have an interior volume defined by a bottom surface and at least one side wall extending from the bottom surface to an open upper end, a liver-derived layer that contains a test anti-cancer agent and is in direct contact with the bottom surface, and a volume of cell culture media. The one or more bone marrow cells can be adjacent the liver-derived layer. Next, an insert can be transferred from the interior volume of the first well into a second well. The insert can include a lower surface comprising a semi-permeable membrane and at least one side wall extending from the lower surface to define an insert chamber, at least one tumor cell located in the insert chamber and configured to express a detectable marker, and at least one support cell located in the insert chamber. The second well can have an interior volume defined by a bottom surface and at least one side wall extending from the bottom surface to an open upper end, a liver-derived layer that is free of the test anti-cancer agent and is in direct contact with the bottom surface, one or more bone marrow cells adjacent the liver-derived layer, and a volume of cell culture media. After a second period of time, the viability of the at least one tumor cell can be determined based on a signal generated by the detectable marker. A decrease in the detected signal and viability of the one or more bone marrow cells, as compared to a control, can be indicative of a candidate anti-cancer agent.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Definitions

Figure 1:
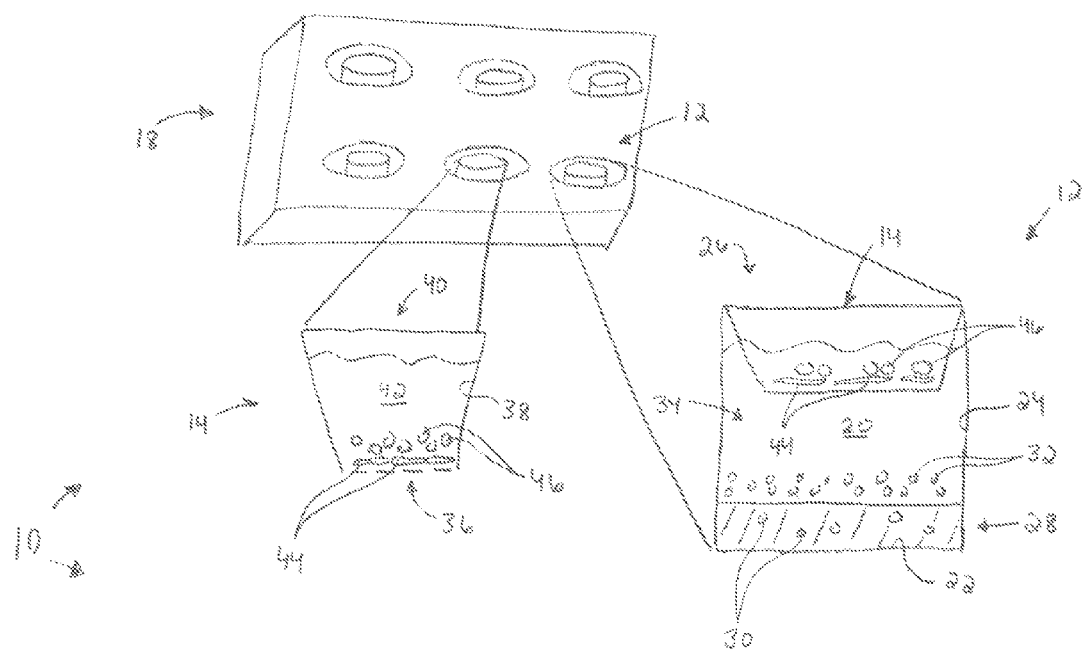
FIG. 1 is a schematic illustration showing an in vitro assay system for identifying a candidate anti-cancer agent constructed in accordance with one aspect of the present disclosure.
Figure 1:
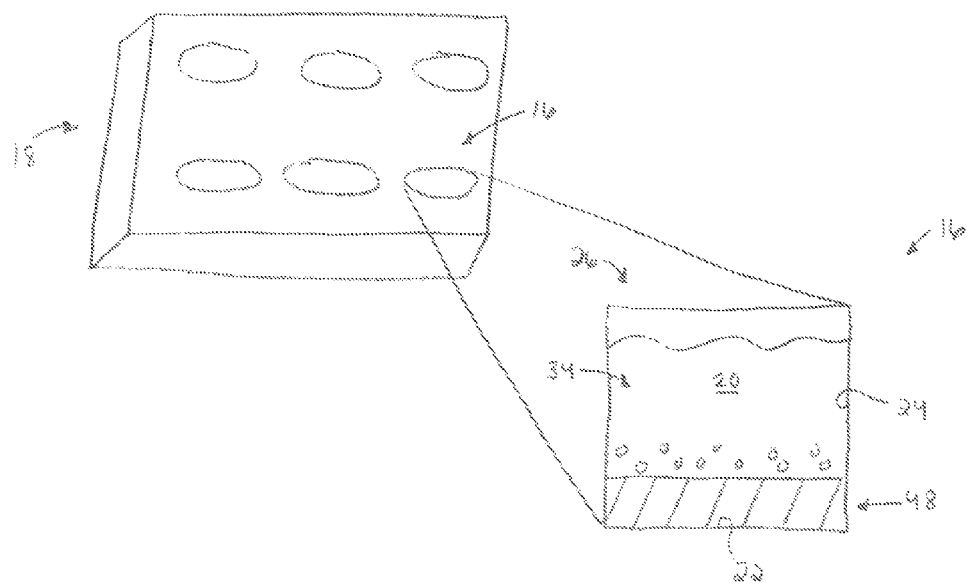

Unless defined otherwise, all technical and scientific terms used herein have the same meaning as is commonly understood by one of skill in the art to which the present disclosure pertains.

In the context of the present disclosure, the terms "candidate anti-cancer agent" and "test anti-cancer agent" can refer to any compound or agent (e.g., chemotherapeutic compound and/or molecular therapeutic compound), of natural or synthetic origin, that is capable of preventing, reducing the risk of, and/or treating cancer (e.g., by killing tumor cells). The anti-cancer effect may arise through one or more mechanisms, including but not limited to, the regulation of cell proliferation, the inhibition of angiogenesis (the formation of new blood vessels), the inhibition of metastasis (the spread of a tumor from its origin), the inhibition of invasion (the spread of tumor cells into neighboring normal structures), or the promotion of apoptosis (programmed cell death).

As used herein, the term "bone marrow cell" can refer to any allogeneic, autologous, or xenogeneic cell that is obtained or derived from the bone marrow of a subject either directly (e.g., by aspiration and isolation from bone marrow) or indirectly (e.g., by isolation from bone marrow followed by subsequent differentiation). A bone marrow cell can include both primary bone marrow tissue and bone marrow cell lines from mammals, such as primates and humans, as well as precursor cells. Bone marrow cells may include, in addition to leukocytes, progenitor cells, such as stem cells.

As used herein, the term "cell culture media" can refer to any one or combination of supplemented or non-supplemented solutions capable of promoting or providing growth, maintenance, differentiation, transfection, and/or propagation of cells, tissues, or their products.

As used herein, the term "tumor cell" can refer to a cell that has been derived from a tumor. The tumor cell can be from a primary tumor or it can be from a tumor that has metastasized.

The tumor cell can also be from a tumor cell line. Tumor cell lines are widely available and can be obtained from many companies including, but not limited to, ATCC (American Type Culture Collection, Rockville, Md.).

As used herein, the term "detectable marker" can refer to any chemical or biological compound, agent, or moiety that is capable of detection (e.g., by observation using microscopy or other imaging modality).

As used herein, the term "subject" can be used interchangeably with the term "patient" and refer to any warm-blooded organism including, but not limited to, human beings, pigs, rats, mice, dogs, goats, sheep, horses, monkeys, apes, farm animals, livestock, rabbits, cattle, etc.

As used herein, the term "apparently healthy subject" can refer to a subject that has not previously been diagnosed as having any signs or symptoms indicating the presence of a disease or disorder, such as cancer. Apparently healthy subjects may not otherwise exhibit symptoms of a particular disease or disorder. In other words, such subjects, if examined by a medical professional, would be characterized as being healthy and free of symptoms of a particular disease or disorder (e.g., cancer).

As used herein, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "directly adjacent" another feature may have portions that overlap or underlie the adjacent feature, whereas a structure or feature that is disposed "adjacent" another feature may not have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of a device in use or operation, in addition to the orientation depicted in the figures. For example, if a device in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

Overview

The present disclosure relates generally to drug discovery and development and, more particularly, to in vitro assay systems and methods for selecting lead anti-cancer agents for subsequent testing in human and non-human subjects. In the field of new drug development, traditional studies tend to focus on the effect of a candidate compound on a specific cell type of interest, in isolation from the general biological context in which the cell functions. In other words, this type of study, for various reasons, intentionally or accidentally omits the microenvironment in which the cell operates, and thus it may not come as a surprise when one identifies a promising drug candidate in the initial in vitro study, only to find in later stage drug development that the candidate drug fails in clinical trial. Also in the field of new drug development, extensive animal testing is required before a candidate compound can proceed to human trials. Besides the ethical considerations involved with such testing, the process is a very costly one that may not be entirely reliable as the reaction of a candidate drug in an animal's body may be quite different from the reaction in a human.

Advantageously, the present disclosure includes in vitro assay systems and methods that simulate drug clearance by liver and kidney and provides anti-cancer activity and bone marrow toxicity readout in the context of cancer stromal support and cellular diffusion barriers. With a relatively simple setup, the systems and methods of the present disclosure mimic four organ systems—liver, kidney and other non-hepatic clearance, micro-environmental stromal support, and cellular diffusion barriers (as in blood vessels and gastrointestinal mucosa)—that are crucial for assessing in vivo activity of candidate anti-cancer agents. The present disclosure advantageously aids in the selection of candidate anti-cancer agents for animal testing, thereby reducing the amount of futile animal experiments. As discussed in more detail below, the present disclosure allows filtering for candidate anti-cancer agents that are not inactivated by liver enzymes, are able to diffuse through cell layers, are not toxic to bone marrow cells, retain anti-cancer activity in the context of stromal support, and are effective after time-limited exposure mimicking non-hepatic clearance by kidneys and other mechanisms.

In Vitro Assay Systems

One aspect of the present disclosure can include an in vitro assay system 10 (FIG. 1) for identifying a candidate anti-cancer agent. The system 10 can comprise a first well 12, a removable insert 14, and a second well 16. The first 12 and second wells 16 can comprise part of the same or different multiwell plate 18. Although a 6-well plate 18 is shown in FIG. 1, it will be appreciated that the first and second wells 12 and 16 can comprise part of the same or different multiwell plate having, e.g., 12-, 24-, 48-, or 96-wells (or more). Multiwell plates 18 are commercially available from a variety of sources, such as Sigma-Aldrich Co. LLC (St. Louis, Mo.). Each of the first and second wells 12 and 16 can have an interior volume 20 defined by a bottom surface 22 and at least one side wall 24 that extends from the bottom surface to an open upper end 26 of each well. Although the first and second wells 12 and 16 are illustrated in FIG. 1 as having a single circular side wall 24, it will be appreciated that each well can have any number of side walls. Regardless of well sizes, sample volume, or other assay parameters, it is a feature of the present disclosure that the system 10 (and associated methods) is in a scalable format that can be carried out in large numbers or high-throughput with ease; although, individual experiments or assays using the system need not always be carried out in high-throughput.

In another aspect, the first well 12 can comprise a liver-derived layer 28 that contains a test anti-cancer agent 30, one or more bone marrow cells 32, and a volume of cell culture media 34 disposed therein. The liver-derived layer 28 can be in direct contact with the bottom surface 22 of the first well 12. The liver-derived layer 28 can comprise a liver homogenate or liver extract that is derived from a subject to be used during in vivo testing of the test anti-cancer agent 30. In some instances, the liver-derived layer 28 can be formulated to further include a low melting temperature agarose. In one example, the liver-derived layer 28 can comprise mouse liver homogenate prepared with about 1% low melting temperature agarose and mixed with a test anti-cancer agent 30. Advantageously, the presence of the liver-derived layer 28 permits selection of candidate anti-cancer agents 30 that are not inactivated by liver enzymes.

In another aspect, the first well 12 can include one or more bone marrow cells 32 located adjacent the liver-derived layer 28. In some instances, the bone marrow cells 32 can comprise a continuous or discontinuous cell layer, at least part of which is in direct contact with the liver-derived layer 28. The bone marrow cells 32 can be derived from an apparently healthy subject. In some instances, the bone marrow cells 32 can be obtained from a commercial source or from discarded bags of apparently healthy bone marrow donors. It will be appreciated that bone marrow cells 32 for use with the system 10 can be freshly obtained or may be frozen prior to use. Advantageously, the presence of the bone marrow cells 32 permits screening for anti-cancer agents 30 that are non-toxic to such cells.

In another aspect, the first well 12 can include a volume of cell culture media 34 disposed in its interior volume 20. The particular volume of cell culture media 34 will vary depending on the size of the first well 12; however, it will be appreciated that the volume of cell culture media will at least be sufficient to promote or provide growth, maintenance, differentiation, transfection, and/or propagation of the cells disposed therein. Similarly, the type of cell culture media 34 (and its particular formulation) will be vary depending upon the nature of cells, their desired growth characteristics and/or phenotypes, cell densities, and the like. Non-limiting examples of cell culture media 34 are known in the art and can include balanced salt solutions (e.g., PBS, DPBS, HBSS, EBSS), basal media (e.g., MEM, DMEM), and complex media (e.g., RPMI-1640, IMDM).

In another aspect, the system 10 can include a removable insert 14. The removable insert 14 can include a lower surface 36 comprising a semi-permeable membrane and at least one side wall 38 extending from the lower surface to an open upper end 40 to define an insert chamber 42. The removable insert 14 can be configured to at least partially fit within the first and second wells 12 and 16. Thus, in some instances, the removable insert 14 can have a shape that is complementary to the shape of the first and second wells 12 and 16. In one example, shown in FIG. 1, the insert 14 can have a frustoconical shape. The semi-permeable membrane of the insert 14 can have a permeability sufficient to permit fluid, but not cells, passage therethrough. In one example, pores comprising the semi-permeable membrane can have a diameter that is equal to, or about equal to, 0.4 μm.

The removable insert 14 can additionally comprise one or more stromal support cells 44. The stromal support cells 44 can be entirely or partly adhered to the lower surface 36 of the insert 14. The stromal support cells 44 can include any xenogeneic, allogeneic, or autologous cell type capable of supporting (e.g., providing contact) and/or regulating the growth and/or function of one or more other cell types. The removable insert 14 can include only one type (or population) of stromal support cells 44 or, alternatively, a variety of types (or populations) of stromal support cells depending, at least in part, on the particular cell(s) for which growth support and/or regulation is desired. For instance, stromal support cells 44 may be selected based on the bone marrow cell 32 and/or tumor cell 46 types to be included as part of the system 10. In one example, the stromal support cells 44 can comprise HS-5 cells (obtained, e.g., from the ATCC) for support of MM1.S (multiple myeloma) cells. HS-5 cells secrete the following cytokines: granulocyte colony-stimulating factor (G-CSF); granulocyte-macrophage-CSF (GM-CSF); macrophage-CSF (M-CSF); Kit ligand (KL); macrophage-inhibitory protein-1 alpha, interleukin-1 alpha (IL-1 alpha); IL-1 beta; IL-1 RA, IL-6; IL-8; IL-11; and leukemia inhibitory factor (LIF). Secretion of these cytokines creates a more physiologic environment for the bone marrow cells 32 and confers resistance to myeloma cells (e.g., mainly IL-6).

The removable insert 14 can further comprise at least one tumor cell 46 that is located in the insert chamber 42 and configured to express a detectable marker. The particular type of tumor cell(s) 46 selected for the system 10 can be based, at least in part, on the particular type of cancer for which a candidate anti-cancer agent 30 is being sought. For example, if an anti-cancer agent 30 for leukemia is sought, then the tumor cell 46 selected for use in the system 10 can be myeloma cell. The tumor cell(s) 46 can be associated with the stromal support cells 44. For example, the tumor cell(s) 46 can be in direct contact with the stromal support cells 44 and/or in indirect contact with the stromal support cells (e.g., suspended in a cell culture media 34 in the insert chamber 42, but not in physical contact with the stromal support cells). In some instances, the tumor cell(s) 46 can be xenogeneic, allogeneic, or autologous. In other instances, the tumor cell(s) 46 may be from any mammal, including mouse, rat, pig, goat, cow, monkeys or humans.

The tumor cell(s) 46 may be from an established cancer cell line, adapted for in vitro culturing, or from a primary tissue sample. Cells from any tumor type may be used in the system. The tumor may be a solid tumor or a hematological tumor/cancer. Exemplary solid tumors include but are not limited to: sarcoma or carcinoma of the bone, cartilage, soft tissue, smooth or skeletal muscle, CNS (brain and spinal cord), peripheral nervous system (PNS), head and neck, esophagus, stomach, small or large intestine, colon, rectum, GI tract, skin, liver, pancreas, spleen, lung, heart, thyroid, endocrine or exocrine glands, kidney, adrenals, prostate, testis, breast, ovary, uterus, cervix, etc. Exemplary hematological/blood cancers include but are not limited to: leukemia (such as adult or childhood Acute Lymphoblastic Leukemia (ALL), adult or childhood Acute Myeloid Leukemia (AML), Chronic Lymphocytic Leukemia (CLL), Chronic Myelogenous Leukemia (CML), Hairy Cell Leukemia), lymphoma (such as AIDS-Related Lymphoma, adult or childhood Hodgkin's Lymphoma, adult or childhood Non-Hodgkin's Lymphoma, T-Cell Lymphoma, or Cutaneous Lymphoma), myeloproliferative disorders (e.g., polycythemia vera, essential thrombocythemia, chronic idiopathic myelofibrosis), myelodysplastic syndromes, e.g., essential thrombocytemia, polycythemia vera, or Multiple Myeloma (MM). It will be appreciated that the tumor cell(s) 46 may be from non-malignant tumors, such as adenoma, chondroma, enchondroma, fibroma, myoma, myxoma, incidentaloma, benign neurinoma, osteoblastoma, osteochondroma, osteoma, papillary tumor, papillary tumour, papilloma, villoma, etc.

The tumor cell(s) 46 can be configured to express one or more detectable markers. Thus, in some instances, the tumor cell(s) 46 can include cells having one or more genetic manipulations (or be genetically modified) to express the one or more detectable markers. Any art-recognized methods may be used to introduce a marker (or markers) into the tumor cell(s) 46 of interest. Examples of such methods are provided in U.S. Patent Application Publication No. 2010/0255999 A1 to Mitsiades et al. In some instances, the choice of marker can depend on the specific biological activity of interest. When it is desirable to detect cell viability (as in methods identifying cytotoxic compounds), the marker can be a biological marker that is detectable only in a living cell 46 and not in dead or unmarked cells. For example, markers whose expression level fluctuates during different stages of the cell cycle, cell maturation, or cell differentiation would not be suitable for such a viability assay.

Useful markers where cell viability is of interest can include, but are not limited to, certain energy-emitting reporter proteins, or certain enzymes, including enzymes in bioluminescent systems, that function in a living cell 46. Alternatively, a marker that is only functional outside the cell 46 may be used to monitor the amount of dead or damaged cells (such as when the marker is released upon cell lysis, and becomes functional once outside the cell). Energy-emitting reporters that are useful in the system 10 of the present disclosure can include light energy-emitting reporters, such as fluorescence- or bioluminescence-emitting reporters. Bioluminescence-emitting reporters can include, for example, enzymes such as luciferase (e.g., firefly luciferase, the Jack-O-Lantern mushroom luciferase, *renilla* luciferase, or luciferase from any of a number of marine creatures) or any one of its modified forms. Fluorescence-emitting reporters can include, for example, GFP (Green Fluorescent Protein), EGFP (Enhanced Green Fluorescent Protein), CFP (Cyan Fluorescent Protein), YFP (Yellow Fluorescent Protein), RFP (Red Fluorescent Protein), BFP (Blue Fluorescent Protein), and their engineered variants. Still other light-emitting proteins that may be useful can include various mutants of GFP with increased fluorescence, color mutants of GFP, such as cyan fluorescent protein (CFP) and yellow fluorescent protein (YFP), employed for, e.g., fluorescence resonance energy transfer (FRET) experiments. Genetically-encoded FRET reporters sensitive to cell signaling molecules, such as calcium or glutamate, protein phosphorylation state, protein complementation, receptor dimerization and other processes may also be useful.

In another aspect, the second well 16 of the system 10 can have an interior volume 20 defined by a bottom surface 22 and at least one side wall 24 extending from the bottom surface to an open upper end 26. The dimensions of the second well 16 can be similar or identical to those of the first well 12. For example, the second well 16 can be adapted to receive the removable insert 14 from the first well 12. The second well 16 can further include a liver-derived layer 48, one or more bone marrow cells 32, and a volume of cell culture media 34. The liver-derived layer 48 can be identically formed and configured as the liver-derived layer 28 in the first well 12, except that the liver-derived layer (of the second well 15) is free of the test anti-cancer agent 30. The bone marrow cells 32 and the cell culture media 34 can be similar or identical to those comprising the first well 12.

Methods

Figure 2:
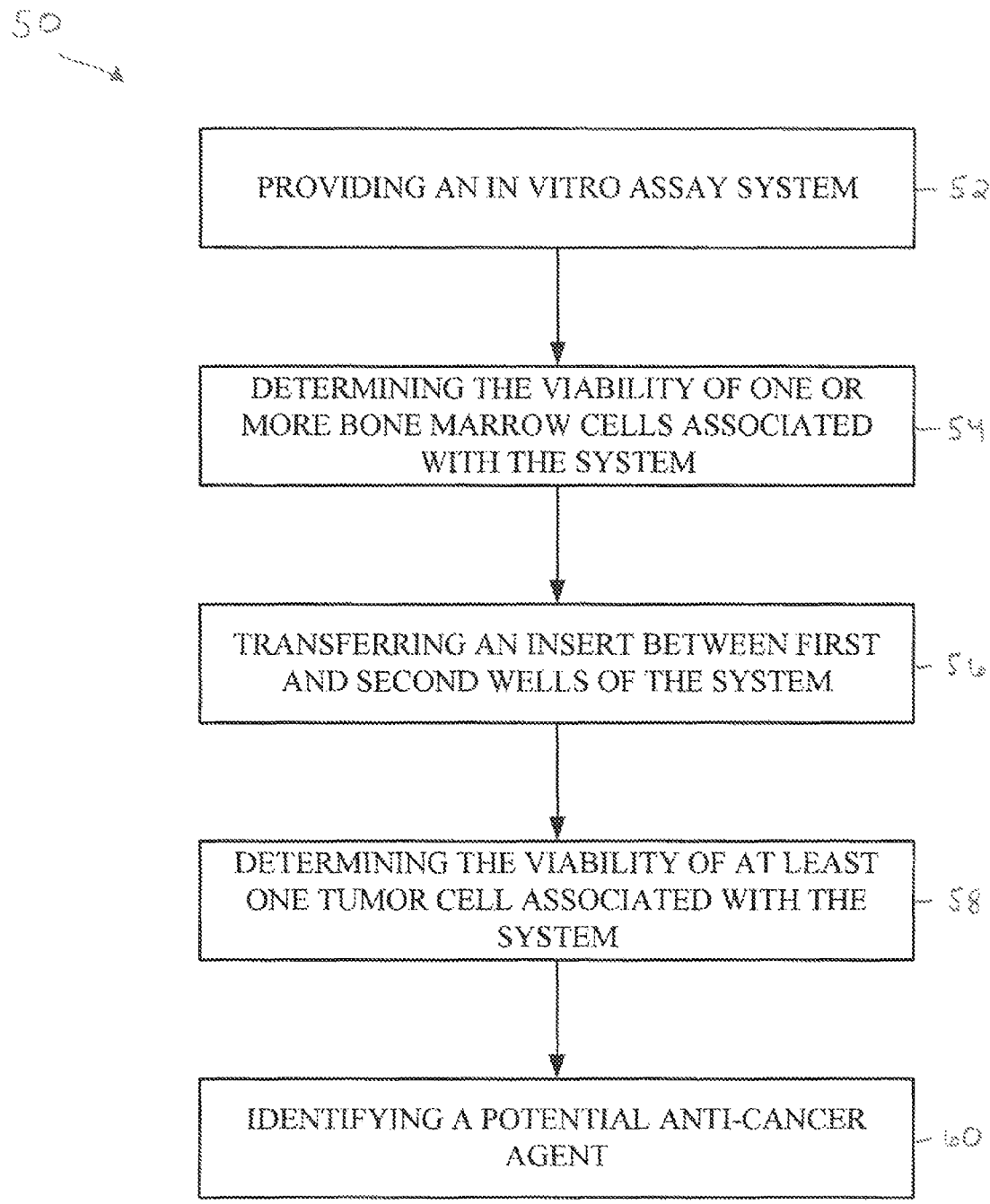
FIG. 2 is a process flow diagram illustrating an in vitro method for identifying a candidate anti-cancer agent according to another aspect of the present disclosure.

Another aspect of the present disclosure can include an in vitro method 50 (FIG. 2) for identifying a candidate anti-cancer agent 30. The method 50 can generally comprise the steps of: providing an in vitro assay system 10 (Step 52); determining the viability of one or more bone marrow cells 32 associated with the system (Step 54); transferring an insert 14 between first and second wells 12 and 16 of the system (Step 56); determining the viability of at least one tumor cell 46 associated with the system (Step 58); and identifying a potential anti-cancer agent (Step 60).

Figure 3:
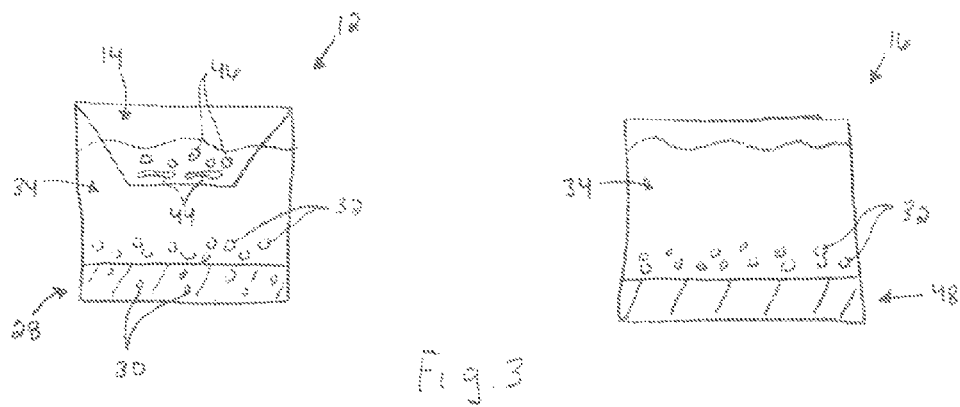
FIG. 3 is a schematic illustration showing a first well and a second well of the system in FIG. 1.

Step 52 of the method 50 can include providing an in vitro assay system 10, such as the one described above. To prepare the system 10, stromal support cells 44 can be grown to confluence on the lower surface 36 of one or more inserts 14. Once the stromal support cells 44 are substantially confluent, one or more tumor cells 46 configured to express a detectable marker (e.g., luciferase) can be added on top of the stromal support cells and then incubated for a period of time (e.g., overnight). Next, a test anti-cancer agent 30 can be mixed with liver homogenate (or liver extract) and incubated (e.g., at about 37° C. for about 30 minutes) before liquid agarose (cooled to about 35-40° C.) is added and solidified at room temperature to form the liver-derived layer 28. For the second well 16, preparation of the liver-derived layer 48 is done in the same manner but without the test anti-cancer agent 30. After preparing the liver-derived layers 28 and 48 for the first and second wells 12 and 16, respectively, cell culture media 34 and bone marrow cells 32 are added to each well. In one example, the bone marrow cells 32 can be obtained from discarded bags of healthy bone marrow donors that were thawed just prior to use with the system 10. A removable insert 14, comprising stromal support cells 44 and tumor cells 46 configured to express a detectable maker, is then placed into the first well 12 (FIG. 3). It will be appreciated that, in an alternative aspect, the second well 16 may not contain a liver-derived layer 48 and bone marrow cells 32 and, rather, the second well may only contain cell culture media 34.

At Step 54, the viability of one or more of the bone marrow cells 32 in the first well 12 can be determined after a period of time (e.g., about 3 days). In one example, viability of the bone marrow cells 32 can be determined by trypan blue exclusion.

Figure 4:
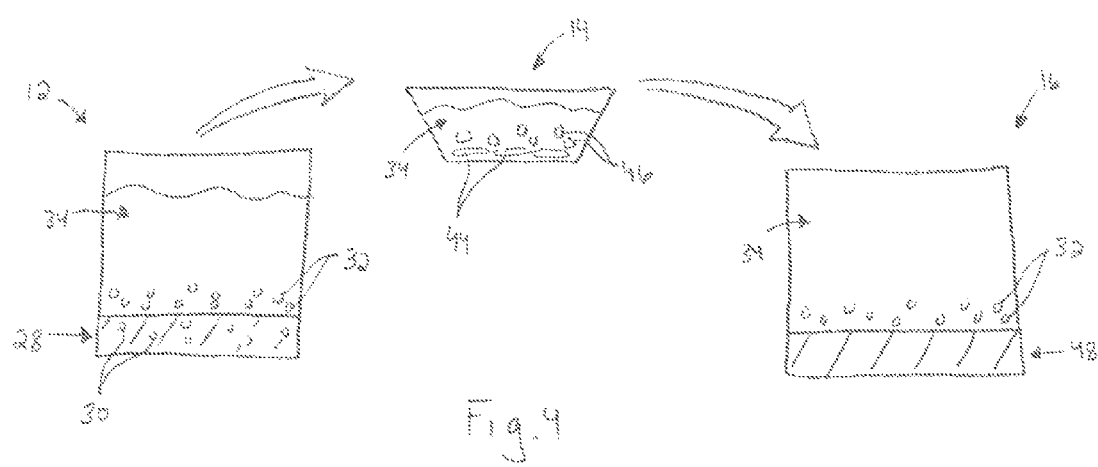
FIG. 4 is a schematic illustration showing an insert being transferred from the first well to the second well in FIG. 3.

Before the bone marrow cells 32 are assessed for viability, the insert 14 can be removed from the first well 12 and placed into the second well 16 at Step 56 (FIG. 4). This can be done, for example, after a period of time that represents kidney clearance (e.g., about 1-5 hours following placement of the insert 14 into the first well 12). It will be appreciated that the bone marrow cells 32 from the first well 12 can optionally be transferred, after washing, to the second well 16.

Figure 5:
FIG. 5 is a schematic illustration showing the insert of FIG. 4 disposed in the second well.

Once the insert 14 has been placed into the second well 16 (FIG. 5), the viability of one or more tumor cells 46 (comprising the insert) can be determined after a second period of time (e.g., about 3 days) (Step 58). The determination can be done, for example, based on a signal generated by the detectable marker. In instances where the detectable marker generates a fluorescent signal, any suitable detection means for detecting such signal may be used, such as a plate reader (not shown). In one example, cell viability can be measured using a CELLTITER-GLO Luminescent Cell Viability Assay (Promega, Madison, Wis.). Data received from the detector (e.g., the plate reader), such as relative or absolute light intensity, may be recorded and stored electronically to allow further data processing, analysis and comparison (e.g., by any suitable software means).

At Step 60, a potential anti-cancer agent 30 can be identified by comparing the viability of the bone marrow cells 32 to a respective control, and also comparing the viability of the tumor cells 46 to a respective control. In some instances, a measured (e.g., statistically significant) decrease in bone marrow cell viability, as compared to a control, and a measured (e.g., statistically significant) increase (or no change) in the viability of the tumor cells 46 can be indicative of a lead anti-cancer agent for subsequent in vivo testing (e.g., in an animal).

From the above description of the present disclosure, those skilled in the art will perceive improvements, changes and modifications. Such improvements, changes, and modifications are within the skill of those in the art and are intended to be covered by the appended claims. All patents, patent applications, and publication cited herein are incorporated by reference in their entirety.

The invention claimed is:

1. An in vitro assay system for identifying a candidate anti-cancer agent, the system comprising:
    (i) a first well having an interior volume defined by a bottom surface and at least one side wall extending from the bottom surface to an open upper end, the first well comprising:
    a liver cell layer that contains a test anti-cancer agent and is in direct contact with the bottom surface;
    one or more bone marrow cells adjacent the liver cell layer; and a volume of cell culture media;
    (ii) a removable insert suspended within the interior volume of the first well and immersed in the volume of cell culture media, the removable insert comprising:
    a lower surface comprising a semi-permeable membrane and at least one side wall extending from the lower surface to define an insert chamber;
    at least one tumor cell located in the insert chamber and expressing a detectable marker; and
    at least one stromal support cell located in the insert chamber; and
    (iii) a second well having an interior volume defined by a bottom surface and at least one side wall extending from the bottom surface to an open upper end, the second well comprising:
    a liver cell layer that is free of the test anti-cancer agent and is in direct contact with the bottom surface;
    one or more bone marrow cells adjacent the liver cell layer; and a volume of cell culture media;
    wherein in use a reduction in detectable signals from the tumor cells while viability of the bone marrow cells in the first well is maintained as compared to a control is indicative of a candidate anti-cancer agent.

2. The system of claim 1, wherein the first well and the second well comprise a single multi-well plate.

3. The system of claim 1, wherein the first well and the second well are located on separate multi-well plates.

4. The system of claim 1, wherein the liver cell layer is one of a liver homogenate or a liver extract.

5. The system of claim 4, further comprising a low melting temperature agarose.

6. The system of claim 4, wherein the liver homogenate or the liver extract is derived from a subject to be used during in vivo testing of the candidate anti-cancer agent.

7. The system of claim 1, wherein the at least one bone marrow cell is derived from an apparently healthy subject.

8. The system of claim 7, wherein the at least one bone marrow cell is autologous or allogeneic.

9. The system of claim 1, wherein the at least one tumor cell is from a tumor cell line.

10. The system of claim 1, wherein the at least one tumor cell is from a tissue sample.

11. The system of claim 10, wherein the tissue sample is from a primary tumor.

12. The system of claim 10, wherein the tissue sample is from a metastatic tumor.

13. The system of claim 1, wherein the at least one tumor cell is from a non-solid tumor.

14. The system of claim 1, wherein the at least one tumor cell is from a solid tumor.

15. The system of claim 1, wherein the at least one tumor cell is a myeloma cell or a leukemia cell.

16. The system of claim 1, wherein the detectable marker is a bioluminescent marker.

17. The system of claim 16, wherein the bioluminescent marker is luciferase.

18. An in vitro method for identifying a candidate anti-cancer agent, the method comprising the steps of:
- determining, after a first period of time, the viability of one or more bone marrow cells present in a first well of the system of claim 1,
- transferring an insert of the system of claim 1 from the interior volume of the first well into a second well of the system of claim 1,
- determining, after a second period of time, the viability of the at least one tumor cell based on a signal generated by the detectable marker;
- wherein a decrease in the detected signal expressed by the at least one tumor cell and viability of the one or more bone marrow cells, as compared to a control, are indicative of a candidate anti-cancer agent.

19. The method of claim 18, wherein the insert is transferred to the second well after a period of time that is representative of non-hepatic clearance.

20. The method of claim 18, wherein the second well, prior to insertion of the insert, only contains cell culture media.

* * * * *